United States Patent
Plaumann et al.

(10) Patent No.: US 7,523,363 B2
(45) Date of Patent: Apr. 21, 2009

(54) METHOD AND TESTER FOR DETERMINING THE ERROR RATE OF A MOBILE RADIO DEVICE WITH VARIABLE BLOCK ALLOCATION

(75) Inventors: Ralf Plaumann, Forstern (DE); Rudolf Schindlmeier, Gilching (DE)

(73) Assignee: Rohde & Schwarz GmbH & Co. KG, Munich (DE)

( * ) Notice: Subject to any disclaimer, the term of this patent is extended or adjusted under 35 U.S.C. 154(b) by 398 days.

(21) Appl. No.: 10/559,395

(22) PCT Filed: Mar. 26, 2004

(86) PCT No.: PCT/EP2004/003251

§ 371 (c)(1),
(2), (4) Date: Dec. 5, 2005

(87) PCT Pub. No.: WO2004/109969

PCT Pub. Date: Dec. 16, 2004

(65) Prior Publication Data

US 2006/0156085 A1    Jul. 13, 2006

(30) Foreign Application Priority Data

Jun. 4, 2003    (DE) .................................. 103 25 288

(51) Int. Cl.
G06F 11/00  (2006.01)
(52) U.S. Cl. ...................................................... 714/704
(58) Field of Classification Search .................. 714/704
See application file for complete search history.

(56) References Cited

U.S. PATENT DOCUMENTS 5,163,051 A * 11/1992 Biessman et al. ........... 714/704

(Continued)

FOREIGN PATENT DOCUMENTS

DE    100 65 937 A1    5/2002

(Continued)

OTHER PUBLICATIONS

"Digital cellular telecommunications system (Phase 2+); Individual equipment type requirements and interworking; Special conformance testing functions (3GPP TS 44.014 version 4.2.0 Release 4); ETSI TS 144 014" ETSI Standards, Jul. 2002, vol. 3-G2, No. V420, European Telecommunications Standards Institute, Sophia-Antipo, FR, XP014010543.

(Continued)

Primary Examiner—James C Kerveros
(74) Attorney, Agent, or Firm—Ditthavong Mori & Steiner, P.C.

(57) ABSTRACT

A method and tester for determining the error rate of a mobile radio device with variable block allocation is provided. Transmission blocks are sent to a mobile radio device to be tested. The mobile radio device to be tested receives and evaluates the transmission blocks and transmits a first and a second qualifier (ack, nack), respectively, for every transmission block correctly or not correctly evaluated. The number of transmission blocks sent to the mobile radio device to be tested and that are not correctly evaluated by the device is determined, and an error rate is determined, the number of transmission blocks being variably set by multiblocks that address the mobile radio device to be tested between one transmission block per multiblock and all transmission blocks of the multiblock and one multiblock comprising a fixed number of transmission blocks.

31 Claims, 4 Drawing Sheets

U.S. PATENT DOCUMENTS

| | | | |
|---|---|---|---|
| 5,910,977 | A | 6/1999 | Torregrossa |
| 6,233,437 | B1 | 5/2001 | Klenner |
| 6,438,717 | B1 * | 8/2002 | Butler et al. ................. 714/704 |
| 6,741,554 | B2 * | 5/2004 | D'Amico et al. ............ 370/225 |
| 6,813,477 | B1 * | 11/2004 | Harris et al. ............. 455/67.14 |
| 6,959,406 | B2 * | 10/2005 | Goldsack et al. ............ 714/704 |
| 7,007,209 | B2 * | 2/2006 | Jaworski ..................... 714/716 |
| 7,181,170 | B2 * | 2/2007 | Love et al. ............... 455/67.13 |
| 7,197,050 | B2 * | 3/2007 | Lucidarme ................. 370/473 |
| 2001/0052091 | A1 | 12/2001 | Goldsack et al. |
| 2007/0165671 | A1 * | 7/2007 | Plaumann et al. ........... 370/473 |

FOREIGN PATENT DOCUMENTS

| | | |
|---|---|---|
| EP | 1 162 776 A1 | 12/2001 |
| WO | WO 02/089390 A1 | 11/2002 |
| WO | PCT/EP2004/003251 | 12/2004 |

OTHER PUBLICATIONS

Gozalvez J et al, "On the effects of correlation in multislot link layer analysis for GPRS" IEEE VTS-FALL VTC 2000. 52$^{nd}$, Sep. 24, 2000, pp. 444-450, XP010525204.

* cited by examiner

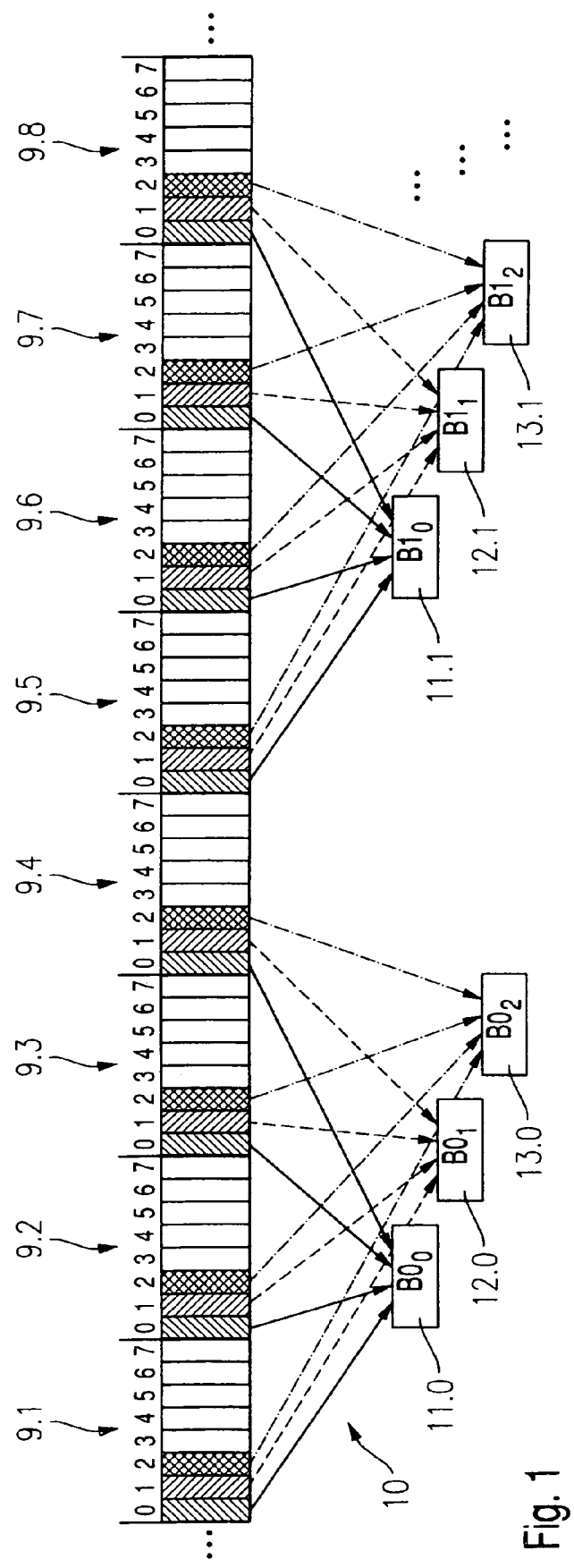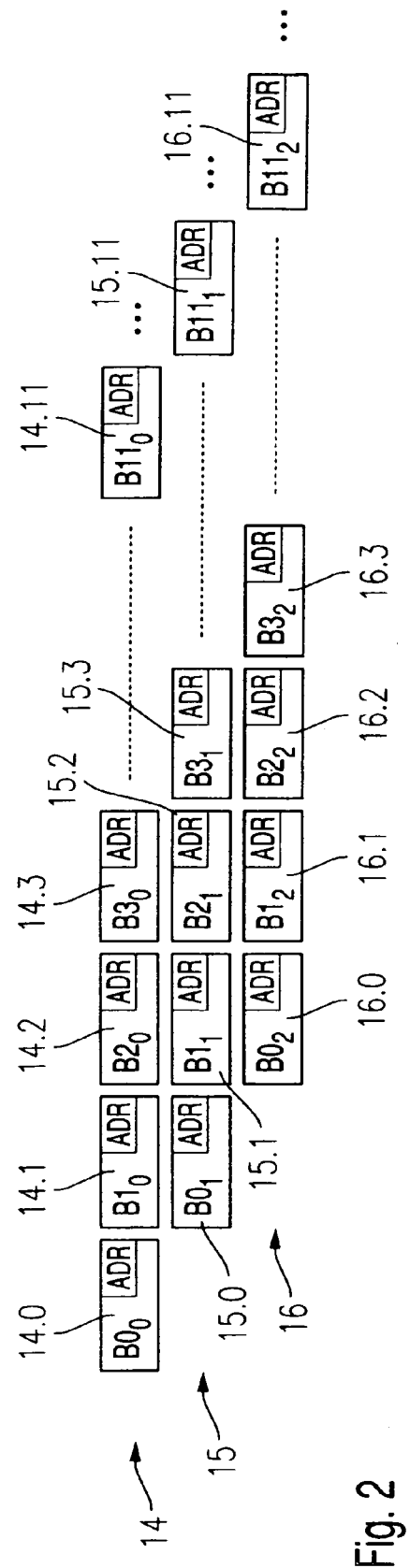
Fig. 1
Fig. 2

METHOD AND TESTER FOR DETERMINING THE ERROR RATE OF A MOBILE RADIO DEVICE WITH VARIABLE BLOCK ALLOCATION

FIELD OF THE INVENTION

The invention relates to a method and a tester for determining an error rate of a mobile-telephone device in the case of a data transfer with variable block assignment.

BACKGROUND OF THE INVENTION

The basic structure of a GSM mobile-telephone system, for example, as described in "Digital Mobile Telephone Systems", Dr.-Ing. Klaus David and Dr.-Ing. Thorsten Benkner, B. G. Teubner Stuttgart 1996, pages 326 to 341, is shown in simplified form in FIG. 5. In a mobile-telephone system of this kind structured according to the GSM standard, a mobile-telephone device, which is disposed, for example, in the motor vehicle 1 illustrated in FIG. 5, communicates with a base station 2.

In order to transmit information between the base station 2 and the mobile-telephone device, a downlink signal 3 is transmitted from the base station 2 to the mobile-telephone device, and an uplink signal 4 is transmitted back from the mobile-telephone device to the base station 2. To keep the downlink signal 3 and the uplink signal 4 separate from one another, both signals are transmitted with different carrier frequencies (e.g., FDD, Frequency Division Duplex).

The transmission of information in the downlink signal 3 and in the uplink signal 4 does not take place in a continuous manner, but in so-called bursts, wherein, eight such bursts of a respective downlink signal 3 or uplink signal 4 together form a frame. In FIG. 5, a downlink frame of this kind is indicated by the reference number 5, and the corresponding uplink frame is indicated by the reference number 6, wherein each burst is transmitted in a timeslot of a frame. The timeslots are numbered continuously from 0 to 7. The downlink frame 5 is transmitted with a first carrier frequency $f_{1DL}$, and the uplink frame 6 is transmitted with a corresponding carrier frequency $f_{1UL}$.

The information is transmitted only in individual bursts of the respective downlink signal 3 or uplink signal 4. For this purpose, one or more given timeslots 0 to 7 of the frame are assigned by the base station 2 to the mobile-telephone device of the motor vehicle 1. Each timeslot 0 to 7 of successive downlink frames 5 and uplink frames 6 forms a transmission channel for the exchange of information between the base station 2 and the mobile-telephone device of the motor vehicle 1. For the first carrier frequency $f_{1DL}$ and the corresponding carrier frequency $f_{1UL}$ of the uplink signal 4, there are therefore eight transmission channels, so that eight mobile-telephone devices can exchange information with the base station 2 independently from one another on this pair of carrier frequencies.

In addition to the first carrier frequency $f_{1DL}$ and the corresponding carrier frequency $f_{1UL}$ for the uplink signal 4, further carrier frequencies are provided for the downlink signal 3, and carrier frequencies corresponding to these are provided for the uplink signal 4. As a result of the TDMA structure with its eight timeslots 0 to 7 in one frame, there are therefore eight transmission channels for each of the 124 carrier-frequency pairs in the context of GSM 900 as illustrated in FIG. 5, wherein all transmission channels are independent of one another. The eight transmission channels for each carrier frequency pair, together with the 124 independent carrier frequency pairs, therefore provide a total of 992 transmission channels.

The use of one transmission channel simultaneously for several mobile-telephone devices to achieve an improved exploitation of the transmission capacity of a mobile telephone system of this kind is already known. Within a transmission channel, the mobile telephones are addressed by a base station, thereby specifying which of the several mobile-telephone devices receives data from the base station in which timeslots.

Corresponding timeslots of four successive frames of the downlink signal 3, or respectively the uplink signal 4, together form a transmission block of the respective transmission channel. For one respective transmission block, which is transmitted from the base station, it can be specified using an address signal ADR, to which of the mobile-telephone devices communicating with the base station in the same transmission channel the transmission block is transmitted from the base station.

Once again, in a simplified form, FIG. 6 illustrates a system of this kind. A total of eight mobile-telephone devices 7, which jointly use one transmission channel in order to communicate with the base station 2, are shown. This means that a given timeslot of the downlink frame 5 and the uplink frame 6 is used for the transmission of information between the mobile-telephone devices 7 and the base station 2. In order to transmit data in a transmission block from the base station 2 to a given mobile-telephone device 8, an address signal ADR, which respectively addresses a given mobile-telephone device 8, is transmitted in each transmission block of the downlink signal 9. By evaluating the address signals ADR, the mobile-telephone device 8 recognizes that the information contained in the transmission block is transmitted to this mobile-telephone device. The other mobile-telephone devices 7 do not recognize the address signal ADR as their own and reject the information of the transmission block. The base station 2 communicates to each mobile-telephone device 7, for example, at the time of establishing the connection, in which of the transmission blocks the mobile-telephone devices 7 actually evaluate an address signal ADR.

In this context, mobile telephones are all subscriber devices, which communicate with the base station 2. The correctness of the data of a transmission block received by the mobile-telephone device 8 is checked, for example, using a checksum. For each of the received transmission blocks, which were addressed to the mobile-telephone device 8, the base station 2 is notified on request, which transmission blocks were received and evaluated correctly. At the request of the base station 2, the mobile-telephone device 8 therefore transmits confirmation signals, for example, for each correctly-evaluated transmission block, a first marking "ack" (acknowledged), and for each incorrectly-evaluated transmission block, a second marking "nack" (not acknowledged). To achieve a correct communication of the complete information to the mobile-telephone device 8, each transmission block, for which the base station 2 has received, for example, a second confirmation signal "nack", is re-transmitted.

In developing mobile-telephone devices and in testing devices in production, it is necessary to determine the number of transmission blocks received and evaluated incorrectly and to compare these with the number of transmission blocks transmitted and/or addressed as a whole to this mobile-telephone device. With a given level and given propagation conditions, a permitted maximum threshold of ten per cent (10%)

is provided in the specification, for example, for an EGPRS, for an error rate (BLER, Block Error Rate) determined in this manner.

SUMMARY OF THE INVENTION

There exists a need to provide a method and a tester for determining an error rate, with which the error rate for various requirements of the mobile-telephone device can be determined.

To determine an error rate of a mobile-telephone device in accordance with one aspect of the present invention, transmission blocks are transmitted to the mobile-telephone device in order to determine whether the mobile-telephone device has received and evaluated these transmission blocks correctly. The number of incorrectly-evaluated transmission blocks, which addressed the mobile-telephone device under test, is determined from the marking "ack" or "nack" transmitted back respectively, and the error rate of the mobile-telephone device is determined from this number.

In evaluating the data contained in a transmission block, the mobile-telephone device is subjected to a particularly large stress, if all of the transmission blocks transmitted contain an address signal ADR, which addresses the mobile-telephone device under test. The number of transmission blocks of a multiblock, which address the mobile-telephone device under test, is therefore specified according to one aspect of the invention. In this context, a multiblock includes a fixed number of successive transmission blocks of a transmission channel. As a result of this variable specification of the number of transmission blocks with an address signal ADR, which addresses the mobile-telephone device under test, the stress on the mobile-telephone device under test can be influenced in a targeted manner. For example, evaluations regarding an increase in the error rate with increasing stress are therefore also possible.

Still other aspects, features, and advantages of the present invention are readily apparent from the following detailed description, simply by illustrating a number of particular embodiments and implementations, including the best mode contemplated for carrying out the present invention. The present invention is also capable of other and different embodiments, and its several details can be modified in various obvious respects, all without departing from the spirit and scope of the present invention. Accordingly, the drawings and description are to be regarded as illustrative in nature, and not as restrictive.

BRIEF DESCRIPTION OF THE DRAWINGS

The invention is described in detail in the description below with reference to the drawings. The drawings are as follows:

FIG. 1 shows a schematic presentation of a signal transmitted from a base station to a mobile-telephone device, FIG. 2 shows a schematic presentation of several transmission blocks respectively in one transmission channel.

DETAILED DESCRIPTION OF THE PREFERRED EMBODIMENT

Figure 3:
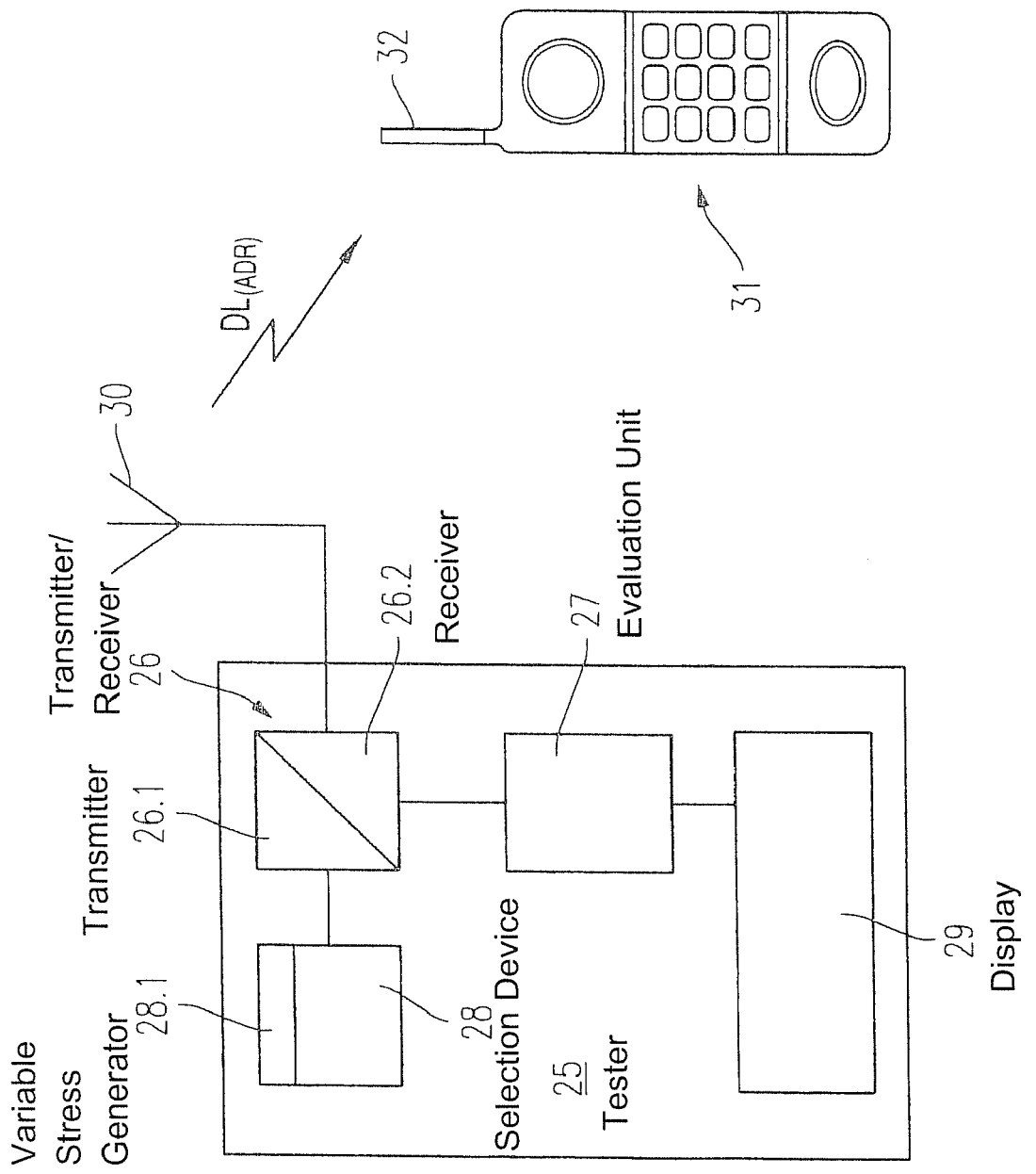
FIG. 3 shows a simplified schematic presentation of a tester according to one aspect of the invention.

FIG. 1 again illustrates the structure of a downlink signal by way of example. The entire signal consists of a concatenation of individual frames, wherein eight frames 9.1 to 9.8 are shown and wherein each frame 9.1 to 9.8 is further subdivided. The frames 9.1 to 9.8 are subdivided into timeslots, wherein eight respective timeslots together form one frame. The individual timeslots are numbered continuously from 0 to 7.

The smallest unit of information, which can be transmitted between the base station 2 and a mobile-telephone device, is formed by one transmission block. A transmission block of this kind includes respectively one given timeslot in four successive frames. By way of example, FIG. 1 shows three examples of transmission blocks of this kind for the first four frames 9.1 to 9.4. A first transmission block 11.0 ($B0_0$) is formed, for example, from the timeslots numbered 0 of the four frames 9.1 to 9.4.

A second transmission block 12.0 ($B0_1$) is formed correspondingly by the timeslots with the number 1 in the same frames 9.1 to 9.4, while the third transmission block 13.0 ($B0_2$) shown in the diagram is formed by the timeslots with the number 2 in the frames 9.1 to 9.4.

Correspondingly, the three further transmission blocks $B1_0$, $B1_1$ and $B1_2$ are formed by the frames 9.5, 9.6, 9.7 and 9.8 with the timeslots numbered 0, 1 and 2. As already explained in the introduction, corresponding timeslots of mutually successive frames 9.1 to 9.8 form a transmission channel, in which a mobile-telephone device communicates with a base station. Accordingly, the illustrated example shows two respective, mutually-successive transmission blocks, 11.0 ($B0_0$) and 11.1 ($B1_0$) for a first transmission channel, 12.0 ($B0_1$) and 12.1 ($B1_1$) for a second transmission channel and 13.0 ($B0_2$) and 13.1 ($B1_2$) for a third transmission channel.

The communication between a mobile-telephone device and the base station 2 is therefore not restricted to a single transmission channel of this kind. On the contrary, in order to increase the quantity of data transmissible between the mobile-telephone device and the base station 2, any number of timeslots 0 to 7 of the frames 9.1 to 9.8 can be used for communication between the mobile-telephone device and the base station 2. The number of timeslots 0 to 7, in which a mobile-telephone device communicates with the base station 2 can therefore vary between one and all of the eight timeslots 0 to 7 of a frame.

For example, all three transmission channels illustrated in FIG. 1 with the transmission blocks 11.0 and 11.1 of the first transmission channel, the transmission blocks 12.0 and 12.1 of the second transmission channel and the transmission blocks 13.0 and 13.1 of the third transmission channel can be used for data transmission between the base station 2 and the mobile-telephone device.

The further time course is shown schematically in FIG. 2, wherein, by way of explanation, the three transmission channels, described with reference to FIG. 1, are shown again as the first transmission channel 14, the second transmission channel 15 and the third transmission channel 16. The individual transmission blocks $B0_0$ to $B11_0$ of the first transmission channel 14 are indicated by the reference numbers 14.0, 14.1 etc. up to 14.11. Correspondingly, the individual transmission blocks $B0_0$ to $B11_1$ of the second transmission channel 15 are indicated by the reference numbers 15.0 to 15.11, and the transmission blocks $B0_2$ to $B11_2$ of the third transmission channel 16 are indicated with the reference numbers 16.0 to 16.11.

For each transmission channel 14, 15 and 16, the illustrated twelve successive transmission blocks 14.0 to 14.11, 15.0 to 15.11 and 16.0 to 16.11 respectively form a multiblock of the corresponding transmission channel 14, 15 and 16. Each of the illustrated transmission blocks $B0_1$ to $B11_1$ is assigned to a given one of the mobile-telephone devices 7 by means of an address signal ADR, which is transmitted in a header of the respective transmission block of the transmission blocks of the downlink signal 9 from the base station 2.

To provide a measure for the quality of the data evaluation of a mobile-telephone device, the number of transmission blocks of the downlink signal incorrectly evaluated by the mobile-telephone device is determined. For this purpose, the corresponding markings, which are transmitted back to the base station by the mobile-telephone device on request from the base station, are evaluated.

For example, with regard to transmission channel 14, the number of transmission blocks 14.0 to 14.1 1, in which the base station 2 transmits to the mobile-telephone device under test is specified according to the invention in a variable manner between only one of the transmission blocks 14.0 to 14.11 and a maximum of all twelve transmission blocks 14.0 to 14.11 of a multiblock of the transmission channel 14. Accordingly, the stress, to which the mobile-telephone device under test is subjected, can be influenced in a targeted manner.

While only a slight stress to the mobile-telephone device under test is caused by isolated transmission blocks addressing the mobile-telephone device under test, because there is a considerable time interval between the individual evaluation algorithms to be implemented by the mobile-telephone device under test, the maximum stress is caused in the evaluation of the transmission blocks 14.0 to 14.11, when determining the error rate, for example, of the first transmission channel 14, with the maximum of twelve transmission blocks 14.0 to 14.11. P By preference, the error rate is determined not only through the evaluation of the number of transmission blocks transmitted in the first transmission channel 14 to the mobile-telephone device under test, but additionally with the use of several timeslots, that is to say, for example, by the additional use of the second transmission channel 15 and the third transmission channel 16 and by also transmitting transmission blocks addressed to the mobile-telephone device under test in these transmission channels. According to one preferred embodiment of the method according to the invention, the number of transmission channels used can also be adjusted in a variable manner between only one transmission channel and all of the transmission channels determined by the timeslots of the frame. In the example of a mobile telephone system provided in the introduction, there are eight transmission channels for the respective eight timeslots 0 to 7 of the frame.

In this context, the number of transmission blocks, which address the mobile-telephone device under test, can be specified separately for the individual transmission channels used. The specification of the transmission channels, in which a communication takes place between the base station 2 and the mobile-telephone device 8, is preferably implemented at the time of establishing the connection. For example, if more transmission blocks are used for the transmission of data from the base station 2 to the mobile-telephone device 8 in order to increase the data rate, a new agreement regarding the transmission channels is made between the mobile-telephone device 8 and the base station 2, which then applies until further instructions.

Figure 4:
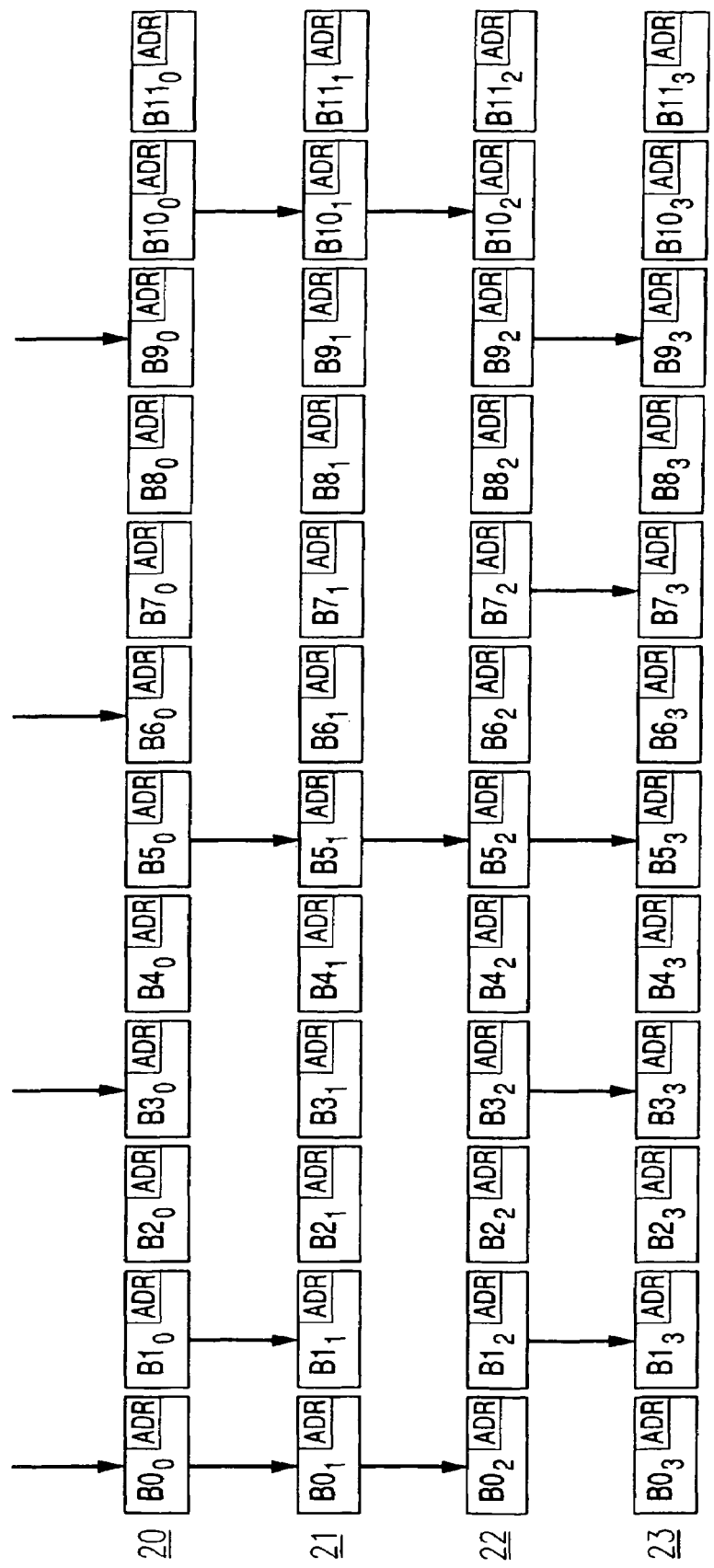
FIG. 4 shows examples for the addressing of a different number of transmission blocks of one multiblock in each case to the mobile-telephone device under test and their different arrangement.
Figure 5:
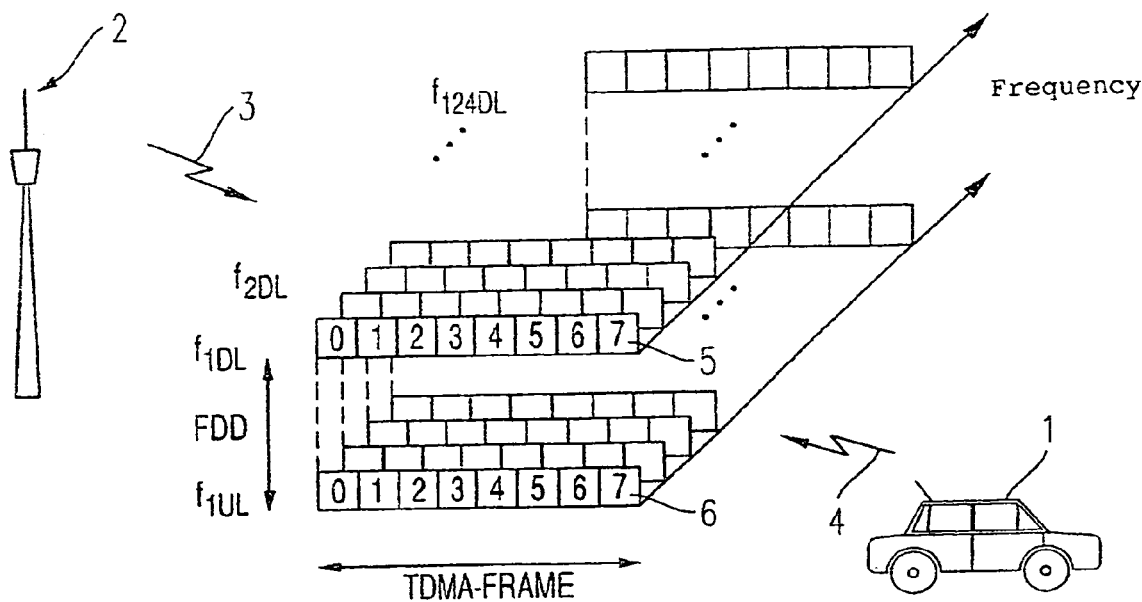
FIG. 5 shows a schematic presentation of the transmission of information in a mobile telephone system according to the GSM standard.
Figure 6:
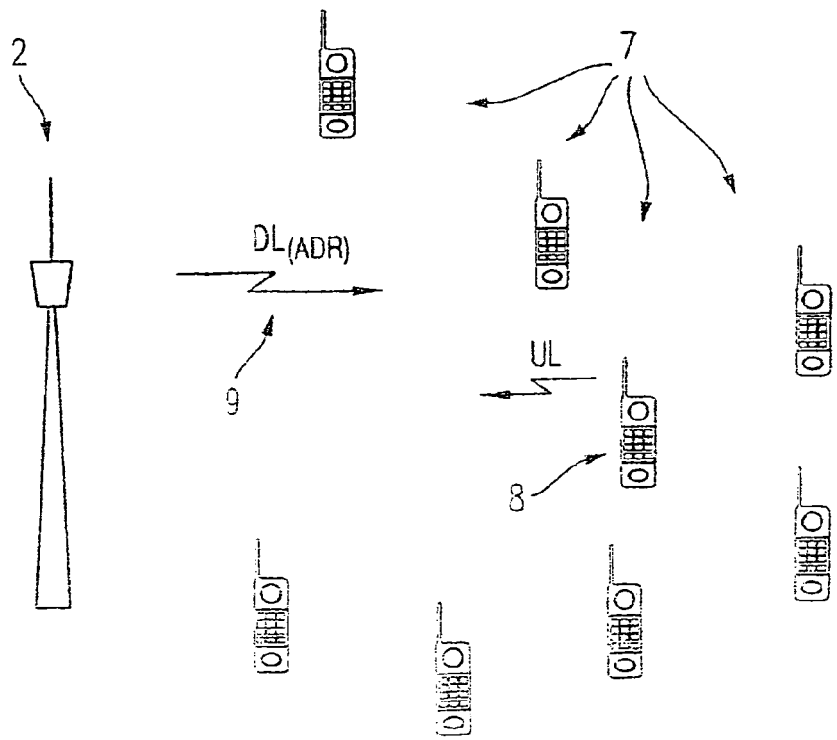
FIG. 6 shows a schematic presentation of the transmission of information between a base station and several mobile-telephone devices in one transmission channel.

By way of example, FIG. 4 shows a mobile-telephone device, for which the error rate is to be determined, in communication with a base station 2 or respectively with a tester emulating a base station, in four transmission channels, which are represented respectively by a multiblock 20, 21, 22 and 23. The schematic structure of a tester of this kind according to the invention is described below with reference to FIG. 3. While, in the first two transmission channels 20 and 21, which are marked with the index "0" and respectively "1" in the individual transmission blocks $B0_1$, to $B0_{11}$, four transmission blocks respectively are transmitted to the mobile-telephone device under test 8, in other words, these transmission blocks contain a corresponding address signal ADR in the header, the transmission channels with the index "2" and respectively "3" contain three or respectively five transmission blocks, which address the mobile-telephone device under test. The transmission blocks, in which data are transmitted from the base station 2 to the mobile-telephone device under test, are indicated with an arrow.

The other transmission blocks can preferably contain dummy data, for example, a predetermined data record without information content. In this context, the association of four timeslots to form one transmission block can also be cancelled. For the transmission blocks, which do not address the mobile-telephone device under test, any measures are permissible in principle, provided it can be ensured that these transmission blocks do not transmit any information to the mobile-telephone device under test. For example, it is also possible to transmit to another mobile-telephone device or to reduce the level.

FIG. 4 also illustrates the possibility of using identical or different patterns for the arrangement of the transmission blocks addressed respectively to the mobile-telephone device under test in different transmission channels, also with an identical number of transmission blocks transmitted to the mobile-telephone device. For example, a uniform arrangement of the four transmission blocks transmitted to the mobile-telephone device under test can take place via the transmission blocks of a multiblock, as illustrated for the multiblock indicated with reference number 20.

However, the transmission blocks $B0_1$ to $B1_{11}$ of a second multiblock 21 which are transmitted to the mobile-telephone device, are distributed in an irregular manner. The arrangement within a multiblock can, for example, be purely random, thereby providing a statistical distribution, which reduces the probability of the occurrence of a systematic error in the implementation of the measurement.

For a third multiblock 22, a uniform distribution of the transmission blocks transmitted to the mobile-telephone device under test is once again illustrated, wherein the number of transmission blocks addressing the mobile-telephone device under test is reduced by comparison with the two multiblocks 20 and 21.

Similarly, the number and the arrangement of the transmission blocks in the multiblock of the individual transmission channels can be selected to be the same for all multiblocks and transmission channels.

In particular, a different arrangement and mutually different numbers of transmission blocks, which address the mobile-telephone device under test, can also be specified for multiblocks of the same transmission channel disposed in time succession relative to one another. This is especially advantageous, if the determination of the error rate is to be defined for variable conditions of the mobile-telephone device.

A tester 25 according to the invention and an arrangement with a mobile-telephone device under test 1 are shown in simplified form in FIG. 3. The tester 25 according to the invention includes a transmitter/receiver device 26, which includes a transmitter device 26.1 for the transmission of a downlink signal and a receiver device 26.2 for receiving an uplink signal transmitted by the mobile-telephone device under test 31 via its antenna 32. Data are transmitted between the mobile-telephone device 31 and the tester 25 either via the antennae 30, 32 or via a connecting cable.

Message signals, that is to say, including the confirmation signals "ack" and respectively "nack", which are transmitted by the mobile-telephone device under test 31, are received by the receiver device 26.2. The receiver device 26.2 is connected to an evaluation unit 27, which registers the number of correctly-evaluated or incorrectly-evaluated transmission blocks of the downlink signal. If only the number of correctly-evaluated transmission blocks is determined, the corresponding number of incorrectly-evaluated transmission blocks can be calculated.

The evaluation unit 27 also comprises a computer unit, which is suitable for determining an error rate for the mobile-telephone device 31 from the number of incorrectly-evaluated transmission blocks.

The error rate determined in the evaluation unit 27 is then displayed on a display device 29. The display on this display device 29 can be provided either by displaying a numerical value or via a corresponding graphic display. Instead of the integrated display device 29, as shown by way of example in FIG. 3, the output may, of course, also be provided on a screen, for example, of a connected computer system.

In order to specify the transmission blocks addressing the mobile-telephone device under test 31, a selection device 28 is also disposed in the tester 25 according to an embodiment of the invention. On the basis of the specifications set by an operator of the tester 25, the selection device 28 defines which transmission blocks of the downlink signal are transmitted via the antenna 30 of the tester 25 or the connecting cable with an address signal ADR addressing the mobile-telephone device under test. In this context, it has already been explained with reference to FIG. 4, that, for different transmission channels and/or for multiblocks transmitted successively, a different number of transmission blocks addressing the mobile-telephone device 31 under test, which can, moreover, be arranged differently within a multiblock, can be transmitted in each case.

The selection device 28 therefore includes means 28.1, with which a respectively variable stress on the mobile-telephone device 31 can be generated. In the simplest case, a memory is provided for this purpose, in which a profile for the successively transmitted multiblocks is stored for each of the transmission channels used, which specifies the number and distribution of the transmission blocks, which are transmitted to the mobile-telephone device under test. In order to determine the number and the distribution of transmission blocks transmitted to the mobile-telephone device under test 31, the number and distribution of address signals ADR addressing the mobile-telephone device for the subsequent multiblocks could also conceivably be calculated from the preceding multiblocks by means of a routine in the selection device 28.

According to one embodiment, in determining the error rate, it is also possible for the base station 2 or respectively the tester 25 used for the implementation and the mobile-telephone device under test to communicate with one another via a sudden-frequency-change process. In this case, the term "transmission channel" relates to the connection between the base station 2 and the mobile-telephone device under test including the sudden-frequency change. This means that the transmission channel is then continued with the new carrier frequency, and the specification of the number of transmission blocks, which addresses the mobile-telephone device under test, does not take the respective sudden-frequency change into consideration.

While the present invention has been described in connection with a number of embodiments and implementations, the present invention is not so limited but covers various obvious modifications and equivalent arrangements, which fall within the purview of the appended claims.

The invention claimed is:

1. A method for determining an error rate in a data transfer to a mobile-telephone device, comprising the steps of:
   transmitting transmission blocks to the mobile-telephone device under test;
   receiving and evaluating the transmission blocks by the mobile-telephone device under test;
   transmitting a first or a second marking by the mobile-telephone device under test for a correctly-evaluated transmission block or respectively an incorrectly-evaluated transmission block;
   determining a number of transmission blocks, which were transmitted to the mobile-telephone device under test, and which were incorrectly evaluated by the mobile-telephone device under test; and
   determining an error rate based on the number of incorrectly-evaluated transmission blocks, wherein the number of transmission blocks of multiblocks, which address the mobile-telephone device under test, is specified in a manner such that the stress to which the mobile-telephone under test is subjected is influenced in a targeted manner between one transmission block per multiblock and all of the transmission blocks of the multiblock, wherein a multiblock includes a fixed number of transmission blocks.

2. A method according to claim 1, wherein one or more transmission blocks of a plurality of transmission channels respectively are addressed to the mobile-telephone device under test.

3. A method according to claim 2, wherein the number or the arrangement of the transmission blocks of a multiblock, which are transmitted to the mobile-telephone device under test, is specified for each of the transmission channels.

4. A method according to claim 2, wherein at least one transmission block of a multiblock is transmitted to the mobile-telephone device under test for each transmission channel used by the mobile-telephone device under test.

5. A method according to claim 1, wherein the number of transmission blocks transmitted to the mobile-telephone device under test is constant for multiblocks of the same transmission channel disposed in time succession.

6. A method according to claim 1, wherein the number of transmission blocks transmitted to the mobile-telephone device under test is varied for multiblocks of the same transmission channel disposed in time succession relative to one another.

7. A method according to claim 1, wherein the transmission blocks transmitted to the mobile-telephone device under test are arranged approximately uniformly within a multiblock.

8. A method according to claim 1, wherein the transmission blocks addressed to the mobile-telephone device under test are arranged randomly within a multiblock.

9. A tester for determining an error rate in a data transmission to a mobile-telephone device, comprising:
a transmitter configured to transmit transmission blocks;
a receiver configured to receive first and second markings transmitted by the mobile-telephone device under test;
an evaluation device configured to determine a number of transmission blocks incorrectly evaluated by the mobile-telephone device under test based on the first and second markings received and to determine an error rate from the number of incorrectly-evaluated transmission blocks; and
a selection device for specifying in a manner such that the stress to which the mobile-telephone under test is subjected is influenced in a targeted manner the number of transmission blocks of a multiblock, which address the mobile-telephone device under test, between one transmission block per multiblock and all of the transmission blocks per multiblock, wherein a multiblock includes a fixed number of transmission blocks.

10. A tester according to claim 9, wherein the selection device comprises means for addressing one or more transmission blocks of a plurality of transmission channels to the mobile-telephone device under test.

11. A tester according to claim 10, wherein the selection device comprises means for specifying, separately for each of the several transmission channels, the number or the arrangement of the transmission blocks, which address the mobile-telephone device under test.

12. A tester according to claim 9, wherein the number of transmission blocks, which address the mobile-telephone device under test, is varied by the selection device for multiblocks disposed in time succession relative to one another.

13. A tester according to claim 9, wherein the selection device comprises means for the uniform arrangement of the transmission blocks of a multiblock, which address the mobile-telephone device.

14. A tester according to claim 9, wherein the selection device comprises means for the random affangement of the transmission blocks of a multiblock, which address the mobile-telephone device.

15. A method for determining an error rate in a data transfer to a mobile-telephone device, comprising the steps of:
transmitting transmission blocks which are addressed to the mobile-telephone device under test and belong to successively sent multiblocks to the mobile-telephone device under test, whereby each multiblock includes a fixed number of successive transmission blocks;
receiving and evaluating the transmission blocks which are addressed to the mobile-telephone device under test by the mobile-telephone device under test;
transmitting a first or a second marking by the mobile-telephone device under test for a correctly-evaluated transmission block or respectively an incorrectly-evaluated transmission block;
determining a number of transmission blocks, which were transmitted and addressed to the mobile-telephone device under test, and which were incorrectly evaluated by the mobile-telephone device under test; and
determining an error rate based on the number of incorrectly-evaluated transmission blocks in relation to the number of the transmission blocks transmitted and addressed as a whole to the mobile-telephone device under test, wherein the number of transmission blocks of multiblocks, which address the mobile-telephone device under test, is specified in a variable manner such that the number of transmission blocks transmitted and addressed to the mobile-telephone device under test is varied for multiblocks of the same transmission channel disposed in time succession relative to one another and the transmission blocks addressed to the mobile-telephone device under test are arranged randomly within a multiblock.

16. A method according to claim 15, wherein one or more transmission blocks of a plurality of transmission channels respectively are transmitted and addressed to the mobile-telephone device under test.

17. A method according to claim 16, wherein the number or the arrangement of the transmission blocks of a multiblock which are transmitted and addressed to the mobile-telephone device under test is specified for each of the transmission channels.

18. A method according to claim 16, wherein at least one transmission block of a multiblock is transmitted to the mobile-telephone device under test for each transmission channel used by the mobile-telephone device under test.

19. A tester for determining an error rate in a data transmission to a mobile-telephone device, comprising:
a transmitter configured to transmit transmission blocks which are addressed to the mobile-telephone device under test and belong to successively sent multiblocks, whereby each multiblock includes a fixed number of successive transmission blocks;
a receiver configured to receive first and second markings transmitted by the mobile-telephone device under test;
an evaluation device configured to determine a number of transmission blocks incorrectly evaluated by the mobile-telephone device under test based on the first and second markings received and to determine an error rate from the number of incorrectly-evaluated transmission blocks in relation to the number of the transmission blocks transmitted and addressed as a whole to the mobile-telephone device under test; and
a selection device for specifying in a variable manner the number of transmission blocks of multiblocks which address the mobile-telephone device under test between one transmission block per multiblock and all of the transmission blocks per multiblock, wherein the selection device comprises means for varying the number of transmission blocks which address the mobile-telephone device under test for multiblocks disposed in time succession relative to one another and for the random arrangement of the transmission blocks of a multiblock which address the mobile-telephone device under test.

20. A tester according to claim 19, wherein the selection device comprises means for addressing one or more transmission blocks of a plurality of transmission channels to the mobile-telephone device under test.

21. A tester according to claim 20, wherein the selection device comprises means for specifying, separately, for each of the several transmission channels, the number or the arrangement of the transmission blocks which address the mobile-telephone device under test.

22. A method for determining an error rate in a data transfer to a mobile-telephone device, comprising the steps of:
transmitting transmission blocks which are addressed to the mobile-telephone device under test and belong to successively sent multiblocks to the mobile-telephone device under test, whereby each multiblock includes a fixed number of successive transmission blocks;
receiving and evaluating the transmission blocks which are addressed to the mobile-telephone device under test by the mobile-telephone device under test;

transmitting a first or a second marking by the mobile-telephone device under test for a correctly-evaluated transmission block or respectively an incorrectly-evaluated transmission block;

determining a number of transmission blocks which were transmitted and addressed to the mobile-telephone device under test and which were incorrectly evaluated by the mobile-telephone device under test; and determining an error rate based on the number of incorrectly-evaluated transmission blocks in relation to the number of the transmission blocks transmitted and addressed as a whole to the mobile-telephone device under test, wherein the number of transmission blocks of multiblocks which address the mobile-telephone device under test is specified in a variable manner such that the number of transmission blocks transmitted and addressed to the mobile-telephone device under test is varied for multiblocks of the same transmission channel disposed in time succession relative to one another and for each of the transmission channels the number and the arrangement of the transmission blocks transmitted and addressed to the mobile-telephone device under test are selected to be the same and the transmission blocks addressed to the mobile-telephone device under test are arranged randomly within a multiblock.

23. A method according to claim 22, wherein one or more transmission blocks of a plurality of transmission channels respectively are transmitted and addressed to the mobile-telephone device under test.

24. A method according to claim 23, wherein at least one transmission block of a multiblock is transmitted and addressed to the mobile-telephone device under test for each transmission channel used by the mobile-telephone device under test.

25. A tester for determining an error rate in a data transmission to a mobile-telephone device, comprising:

a transmitter configured to transmit transmission blocks which are addressed to the mobile-telephone device under test and belong to successively sent multiblocks, whereby each multiblock includes a fixed number of successive transmission blocks;

a receiver configured to receive first and second markings transmitted by the mobile-telephone device under test;

an evaluation device configured to determine a number of transmission blocks incorrectly evaluated by the mobile-telephone device under test based on the first and second markings received and to determine an error rate from the number of incorrectly-evaluated transmission blocks in relation to the number of the transmission blocks transmitted and addressed as a whole to the mobile-telephone device under test; and a selection device for specifying in a variable manner the number of transmission blocks of multiblocks which address the mobile-telephone device under test between one transmission block per multiblock and all of the transmission blocks per multiblock, wherein the selection device comprises means for varying the number of transmission blocks which address the mobile-telephone device under test for multiblocks disposed in time succession relative to one another and for selecting for each of the transmission channels the number and the arrangement of the transmission blocks transmitted and addressed to the mobile-telephone device under test to be the same and for the random arrangement of the transmission blocks of a multiblock which address the mobile-telephone device under test.

26. A tester according to claim 25, wherein the selection device comprises means for specifying, separately, for each of the several transmission channels, the number or the arrangement of the transmission blocks which address the mobile-telephone device under test.

27. A method for determining an error rate in a data transfer to a mobile-telephone device, comprising the steps of:

transmitting transmission blocks which are addressed to the mobile-telephone device under test and belong to successively sent multiblocks to the mobile-telephone device under test, whereby each multiblock includes a fixed number of successive transmission blocks;

receiving and evaluating the transmission blocks which are addressed to the mobile-telephone device under test by the mobile-telephone device under test;

transmitting a first or a second marking by the mobile-telephone device under test for a correctly-evaluated transmission block or respectively an incorrectly-evaluated transmission block;

determining a number of transmission blocks which were transmitted and addressed to the mobile-telephone device under test and which were incorrectly evaluated by the mobile-telephone device under test; and determining an error rate based on the number of incorrectly-evaluated transmission blocks in relation to the number of the transmission blocks transmitted and addressed as a whole to the mobile-telephone device under test, wherein the number of transmission blocks of multiblocks which address the mobile-telephone device under test is specified in a variable manner such that the number of transmission blocks transmitted and addressed to the mobile-telephone device under test is varied for multiblocks of the same transmission channel disposed in time succession relative to one another and for each of the transmission channels the number and the arrangement of the transmission blocks transmitted and addressed to the mobile-telephone device under test are selected to be the same and the transmission blocks addressed to the mobile-telephone device under test are arranged randomly within a multiblock and that the increase in the error rate is evaluated in dependence on the number of the transmission blocks of a multiblock transmitted and addressed to the mobile-telephone device under test.

28. A method according to claim 27, wherein one or more transmission blocks of a plurality of transmission channels respectively are transmitted and addressed to the mobile-telephone device under test.

29. A method according to claim 28, wherein at least one transmission block of a multiblock is transmitted and addressed to the mobile-telephone device under test for each transmission channel used by the mobile-telephone device under test.

30. A tester for determining an error rate in a data transmission to a mobile-telephone device, comprising:

a transmitter configured to transmit transmission blocks which are addressed to the mobile-telephone device under test and belong to successively sent multiblocks, whereby each multiblock includes a fixed number of successive transmission blocks;

a receiver configured to receive first and second markings transmitted by the mobile-telephone device under test;

an evaluation device configured to determine a number of transmission blocks incorrectly evaluated by the mobile-telephone device under test based on the first and second markings received and to determine an error rate from the number of incorrectly-evaluated transmission blocks in relation to the number of the transmission blocks transmitted and addressed as a whole to the mobile-telephone device under test; and a selection device for specifying in a variable manner the number of transmission blocks of multiblocks which address the mobile-telephone device under test between one transmission block per multiblock and all of the transmission blocks per multiblock, wherein the selection device comprises means for varying the number of transmission blocks which address the mobile-telephone device under test for multiblocks disposed in time succession relative to one another and for selecting for each of the transmission channels the number and the arrangement of the transmission blocks transmitted and addressed to the mobile-telephone device under test to be the same and for the random arrangement of the transmission blocks of a multiblock which address the mobile-telephone device under test, wherein the selection device is able to evaluate the increase in the error rate in dependence on the number of the transmission blocks of a multiblock transmitted and addressed to the mobile-telephone device under test.

31. A tester according to claim 30, wherein the selection device comprises means for specifying, separately, for each of the several transmission channels, the number or the arrangement of the transmission blocks which address the mobile-telephone device under test.

* * * * *